United States Patent [19]
Brosius

[11] Patent Number: 6,036,489
[45] Date of Patent: Mar. 14, 2000

[54] TORQUED TITANIUM-BASED ARCHWIRE

[75] Inventor: David J. Brosius, Crete, Ill.

[73] Assignee: Ortho Specialties, Inc., Hickory Hills, Ill.

[21] Appl. No.: 09/359,980

[22] Filed: Jul. 23, 1999

[51] Int. Cl.⁷ ..................................... A61C 3/00
[52] U.S. Cl. ............................................... 433/20
[58] Field of Search .................... 433/8, 20, 24

[56] References Cited

U.S. PATENT DOCUMENTS

| | | | |
|---|---|---|---|
| 2,566,414 | 9/1951 | Henry | 433/20 |
| 5,017,133 | 5/1991 | Miura | 433/20 |
| 5,137,446 | 8/1992 | Yamauchi et al. | 433/20 |
| 5,259,760 | 11/1993 | Orikasa | 433/20 |
| 5,683,245 | 11/1997 | Scahdeva et al. | 433/20 |

*Primary Examiner*—Todd E. Manahan
*Attorney, Agent, or Firm*—Leydig Voit & Mayer Ltd.

[57] ABSTRACT

A torqued archwire for use in an edgewise orthodontic bracket system. The archwire is substantially rectangular in cross-section, is made of titanium-based alloy and has a plurality of segments, including an anterior segment which is sized to cooperate with brackets attached to a person's central and lateral teeth. Torque is built into this anterior segment, being maximized at a value of over 21°, and preferably between 21–50° at the centerpoint and adjacent the central teeth brackets and then decreasing continuously along the remaining length of the segment. Extending from the respective ends of the anterior segment is a pair of transition segments, in which the torque built into the archwire diminishes to zero. The lengths of the transition segments are such that these "zero" points occur, in use, between the corresponding adjacent lateral and cuspid brackets. Posterior segments of the archwire, which extend distally from the transition segments, generally include no built-in torque.

18 Claims, 2 Drawing Sheets

TORQUED TITANIUM-BASED ARCHWIRE

TECHNICAL FIELD

The present invention relates to orthodontic systems and appliances, and more particularly, to a titanium-based archwire having a torqued anterior section.

BACKGROUND OF THE INVENTION

Preadjusted and integrated "straight-wire" orthodontic bracket systems are well known, in which all the necessary angles and planes of movement—commonly referred to as "tip," "torque," "in-out" and "anti-rotation"—are manufactured directly into the brackets. These straight-wire appliances, when properly placed on teeth, are designed to allow the force and resilience of unbent archwires to work with the preadjustments to guide the teeth into ideal positions.

Contemporary appliance system designers strive to identify the proper position desired for each tooth at the conclusion of fixed appliance therapy (mechanotherapy), so that the individual brackets can be pre-built to provide, in conjunction with an archwire, theoretically appropriate alignment forces to the respective teeth. For example, if a designer desires seven degrees of crown torque, then a seven degree torque angle has typically been built into the individual edgewise bracket by well-known methods. The amount of torque actually expressed by a bracket, however, is dependent upon the wire-to-slot deviation angle—referred to as slot "play." Some play generally exists between any archwire and an edgewise bracket slot, even if the archwire is considered "full-size" relative to the slot. This play reduces the actual torque provided by the system from its full and theoretically correct expression.

To compensate for inadequate torque built into many preadjusted bracket systems, positive (+) crown torque is commonly added to the upper anterior segment of rectangular or square archwires late in treatment. Similarly, it may be desirable to apply a small amount of lingual or negative (−) crown torque to the lower anterior (i.e., central and lateral) teeth early in treatment to maintain their "upright" orientation.

These anterior-specific torque treatments are handled in various ways. Orthodontists most often add positive crown torque to the upper anterior segment by manually bending the torque into the anterior portion of individual stainless steel archwires. Titanium-based alloy archwires, particularly nickel titanium (nitinol) archwires, are generally considered to be ideal for orthodontics, especially in comparison to stainless steel, largely due to the low force these wires impart to crowns, coupled with their outstanding shape memory. This "superelasticity" is more biocompatible, meaning that there is less chance of damaging the dentition by moving crowns too quickly. Titanium-based wires also provide more complete correction without the need to constantly change archwires due to permanent deformation. It is virtually impossible, however, for an orthodontist to manually bend torque into titanium-based archwires due to this outstanding resistance to permanent deformation. This is why, for the critical final torque moments that are commonly bent into archwires, orthodontists are generally limited to the high forces and low shape memory of stainless steel, as opposed to the far more comfortable and biocompatible forces of nickel titanium or other titanium-based alloys.

For purposes of this invention, it will be understood that the term "titanium-based alloy" is intended to include nickel titanium alloys (with or without other elements, such as copper, columbium, iron or aluminum), beta titanium alloys and near-beta titanium alloys.

Manually bending torque into individual stainless steel archwires is a complex procedure that requires tremendous clinical skill and experience. Even substantial skill and experience do not assure an orthodontist that the desired torque will be imparted to the archwire or that the desired correction will occur precisely for each patient. Moreover, since an orthodontist is almost always directly responsible for manually torquing individual archwires, a great deal of "chairtime" is required.

In regard to applying lingual crown torque to the lower anterior teeth early in the treatment process, this is commonly attempted by using lower anterior brackets which have small amounts of torque built into them. Since small archwires allow for too much "play" in the bracket slots to express low levels of built-in bracket torque, "full-size" archwires are required if there is to be any meaningful expression of the desired lingual torque. Indeed, orthodontists typically increase bracket torque by using a larger bracket wire. Unfortunately, using a large edgewise wire early in treatment is not recommended, since the force provided is likely to be excessive and may cause biocompatibility problems (e.g., an overall reduction in the length of the root of the tooth, referred to as root "resorption"). Likewise, building more torque into the lower anterior brackets to compensate for the archwire play of small wires is not recommended, since problems could arise later in treatment when larger edgewise wires are employed, as they would then begin to express excessive amounts of lingual crown torque.

Because of these various difficulties in anterior-specific torque treatment, pretorqued archwires have been developed in which torque is built directly into the wire during manufacture. Pretorqued wires save valuable chairtime over manual wirebending (particularly since application of them can often be delegated to an orthodontic assistant as a routine wire change), they have greater biocompatibility (if titanium-based wire is used) and they theoretically provide more accurate results.

Currently, two types of pretorqued archwires are available to the orthodontist. One is a preformed stainless steel archwire. These wires have the drawbacks, however, of high force, resultant poor biocompatibility and low shape memory. Also, the built-in torque in all presently known steel versions extends through both the anterior and the posterior segments of the wire. It is not common to add torque to the upper posterior teeth, and it is usually very undesirable to increase torque in the lower posterior teeth. Consequently, the current pretorqued stainless steel archwires are seen as providing little improvement, if any, over the common art of manually bending wires, and they have had very little success in the marketplace.

Pretorqued nickel titanium archwires have also been introduced, but they too have achieved little commercial success since they do not meet certain critical criteria. Specifically, the built-in torque does not appear to be limited to the anterior segment, as is desired for proper treatment. Rather, positive torque appears to extend into the posterior area, where negative crown torque, if any, is most desirable. The transition from passive to torqued (active) wire should ideally occur in the area between the lateral and cuspid brackets (distal to the lateral bracket and mesial to the cuspid bracket), but in the available nitinol pretorqued archwires this transition area is very broad, with the result that too little torque force is imparted to the lateral teeth and/or an undesirable (positive) torque force is imparted to some of the posterior teeth.

U.S. Pat. No. 5,722,827, assigned to ORTHO SPECIALTIES™ discloses a torqued archwire for use in an edgewise orthodontic bracket system. The archwire is substantially rectangular in cross-section, is made of titanium-based alloy and has a plurality of segments, including an anterior segment which is sized to cooperate with brackets attached to a person's central and lateral teeth. Torque is built into this anterior segment, being maximized in a range of about 13–20° at the centerpoint and adjacent the central teeth brackets and then decreasing continuously along the remaining length of the segment. Extending from the respective ends of the anterior segment is a pair of transition segments, in which the torque built into the archwire diminishes to zero. The lengths of the transition segments are such that these "zero" points occur, in use, between the corresponding adjacent lateral and cuspid brackets. Posterior segments of the archwire, which extend distally from the transition segments, generally include no built-in torque.

It has been discovered that torque is sometimes desirable at values greater than can be attained with the system disclosed in U.S. Pat. No. 5,722,827. In efforts to achieve greater torque, orthodontists have used archwire of a larger size, reducing the amount of angular "play," according to the known practice mentioned above.

SUMMARY OF THE INVENTION

It is a primary object of the present invention to provide an improved torqued (i.e., pretorqued) archwire in which built-in torque is limited to a segment of the wire that, in use, corresponds to the brackets attached to anterior teeth.

Another object of the invention is to provide a torqued archwire system which is improved over the system disclosed in U.S. Pat. No. 5,722,827.

Other objects and advantages of the invention will be apparent from the following detailed description.

In accordance with the present invention, there is provided a torqued archwire for use in an edgewise orthodontic bracket system. The archwire is an elongated member (i.e., either a single strand or a multi-strand braid) substantially rectangular in cross-section, is made of titanium-based alloy and has a plurality of segments, including an anterior segment which is sized to cooperate with brackets attached to a person's central and lateral teeth. Torque is built into this anterior segment, being maximized at the centerpoint and adjacent the central teeth brackets and then decreasing continuously along the remaining length of the segment. Extending from the respective ends of the anterior segment is a pair of transition segments, in which the torque built into the archwire diminishes to zero. The lengths of the transition segments are such that these "zero" points occur, in use, between the corresponding adjacent lateral and cuspid brackets. Posterior segments of the archwire, which extend distally from the transition segments, generally include no built-in torque. For ease of reference by an orthodontist, the "active" anterior and transition segments of the archwire are colored with non-toxic ink.

BRIEF DESCRIPTION OF THE DRAWINGS

The detailed description particularly refers to the accompanying figures, in which.

DESCRIPTION OF THE PREFERRED EMBODIMENTS

While the invention will be described in connection with certain preferred embodiments, it will be understood that it is not intended to limit the invention to these particular embodiments. On the contrary, it is intended to cover all alternatives, modifications and equivalents included within the spirit and scope of the invention as defined by the appended claims.

Figure 1:
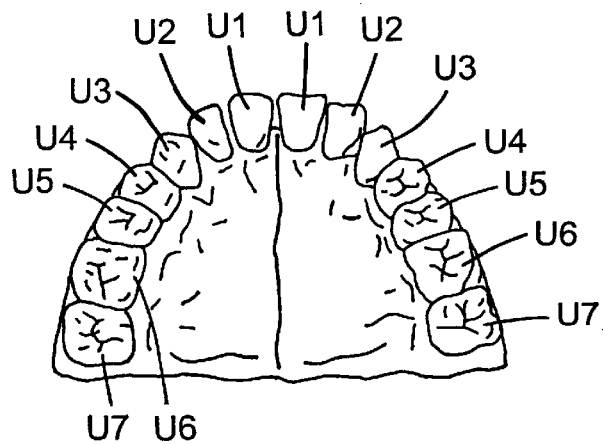
FIG. 1 is a plan view of a set of upper permanent teeth.
Figure 2:
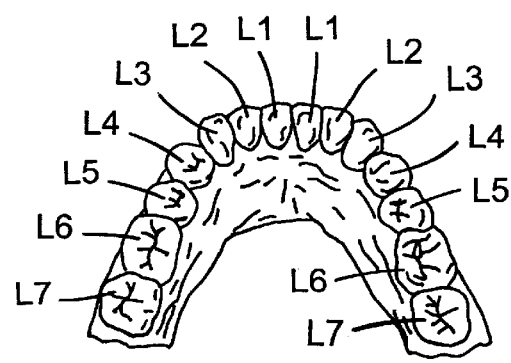
FIG. 2 is a plan view of a set of lower permanent teeth.

Turning now to the drawings and referring first to FIG. 1, there is shown a set of upper (maxillary) permanent teeth, including central teeth (labeled U1), lateral teeth (U2), cuspids (U3), first and second bicuspids (U4 and U5), and first and second molars (U6 and U7). Similarly, FIG. 2 illustrates a set of lower (mandibular) permanent teeth, including central teeth (labeled L1), lateral teeth (L2), cuspids (L3), first and second bicuspids (L4 and L5), and first and second molars (L6 and L7). The centrals and laterals, whether upper or lower, are known collectively as the anteriors.

Figure 3:
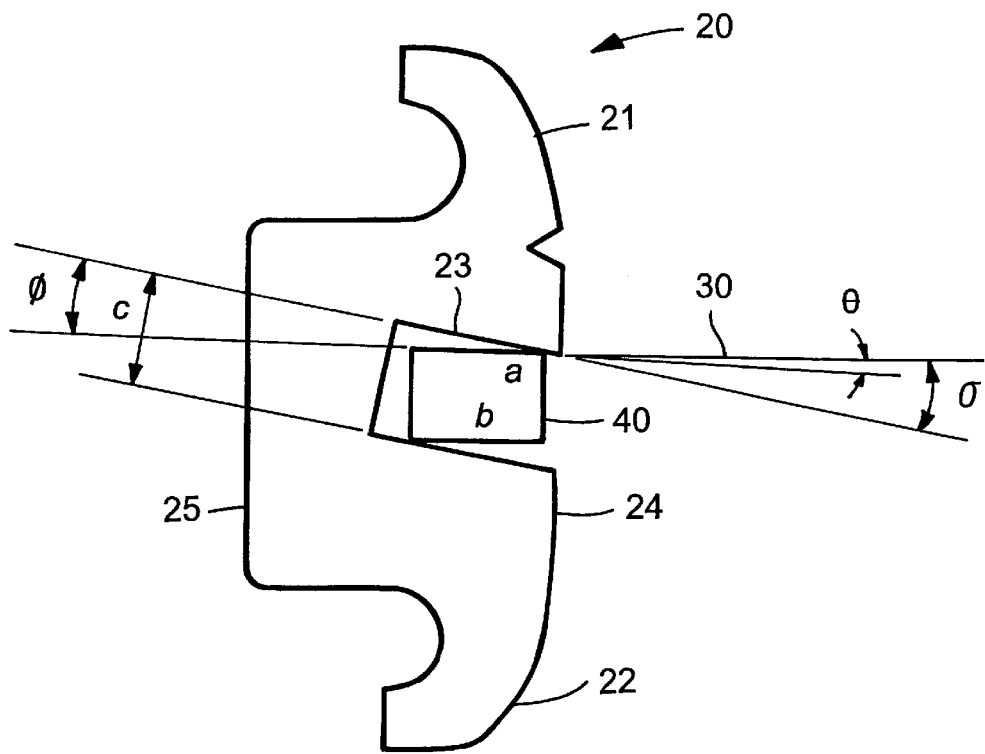
FIG. 3 is a cross-sectional view of an edgewise orthodontic bracket and an archwire, illustrating a plurality of variables used to calculate effective torque angles for an archwire assumed to be perfectly rectangular or square.

The present invention relates to preadjusted orthodontic bracket systems and methods for straightening upper and lower permanent teeth. More specifically, this invention is related to torque, which is also known to orthodontists as inclination or third order bends. Torque inclination is illustrated in FIG. 3. As is well known, an orthodontic bracket 20 includes tie wings 21, 22 and is formed to include a substantially rectangular-shaped slot 23. The bracket includes a front surface 24 and a rear surface 25 designed for attachment to a bonding pad or band, by means of which the bracket is secured on a particular tooth. Slot 23 is formed at a built-in angle σ (known as the torque angle for bracket 20) relative to an imaginary line 30 perpendicular to the rear surface 25 of the bracket. Slot 23 is configured to edgewise receive a substantially rectangular cross-sectioned archwire 40. It should be noted for purposes of the present invention that the term "substantially rectangular archwire" is intended to include both rectangular and square archwire, as well as rectangular and square archwire having "rounded" or "beveled" corners.

The engagement between wire 40 and the side walls defining slot 23 applies a torque force to the tooth on which the bracket is mounted. Different torque angles are typically formed into the respective brackets for various teeth so as to apply a different torque force to each tooth. The built-in torque angle for each tooth depends upon the conventional orthodontic technique for which a bracket is designed.

The torque angle a and the slot width c of a bracket can be designed so that, when the bracket is used with a specifically-manufactured archwire, a conventional orthodontic technique may be replicated as to its theoretically desired embodiment accurately, predictably, efficiently and easily. This is due to precise consideration of the slot width and archwire dimensions (including corner radii) and of the actual torque forces generated. The magnitude of the actual torque forces applied to a tooth is based upon the torque angle σ built into the respective bracket 20, the long cross-sectional dimension b and the short cross-sectional dimension a of the rectangular wire 40, and the width c of the archwire slot 23. The actual (or effective) torque force angle θ is determined by subtracting "slot play" (i.e., the deviation angle φ) in a bracket/wire combination from the built-in torque angle σ. FIG. 3 illustrates these different angles.

The built-in torque angle σ is known (or can be readily determined) for a given bracket, and, if it is assumed that the archwire is perfectly square or rectangular, the $$\phi = \text{ARCSIN}\left[\frac{bc - a\sqrt{a^2 + b^2 - c^2}}{a^2 + b^2}\right].\quad 1$$

deviation angle φ for the bracket/wire combination can be calculated by the formula:

$$\Theta = \sigma - \phi \quad 2$$

Thus, the effective torque angle θ can be easily determined, since

Conversely, it will be appreciated that once the effective torque angle θ recommended by a selected orthodontic technique is determined, and if the precise dimensions of a rectangular archwire and of a bracket slot are measured, then calculations can be made of both the deviation angle φ and the necessary built-in torque angle σ for achieving the effective torque angle.

The formula (1) above, which is based on an assumption of perfectly square or rectangular wire, has been supplemented with more accurate formulas that take into consideration wire corner rounding or beveling, which is common in available archwires. These formulas are discussed in commonly-owned U.S. Pat. No. 5,820,370, issued Oct. 13, 1998, hereby incorporated by reference in its entirety, as if fully restated herein.

Many commercial bracket systems are not designed to compensate for slot play. Instead, brackets are typically designed with the built-in torque angle σ matching the effective torque angle θ prescribed by a particular orthodontic technique. As a result, because "full-sized" wires are not commonly used, the actual torque achieved is usually significantly less than prescribed.

The torqued archwire described herein compensates for the less-than-prescribed torque forces provided by the common usage of commercial bracket systems, particularly in regard to the anterior teeth. Specifically, in accordance with an important aspect of the present invention, a rectangular titanium-based archwire is torqued in a precisely defined anterior region such that, when it is used in conjunction with a commercial bracket system, additional torque force is applied to the anterior teeth. Preferably, the torque built into the archwire should substantially correspond to, and compensate for, the slot play which results from insertion of the archwire into the slots of commercial anterior brackets.

Figure 4:
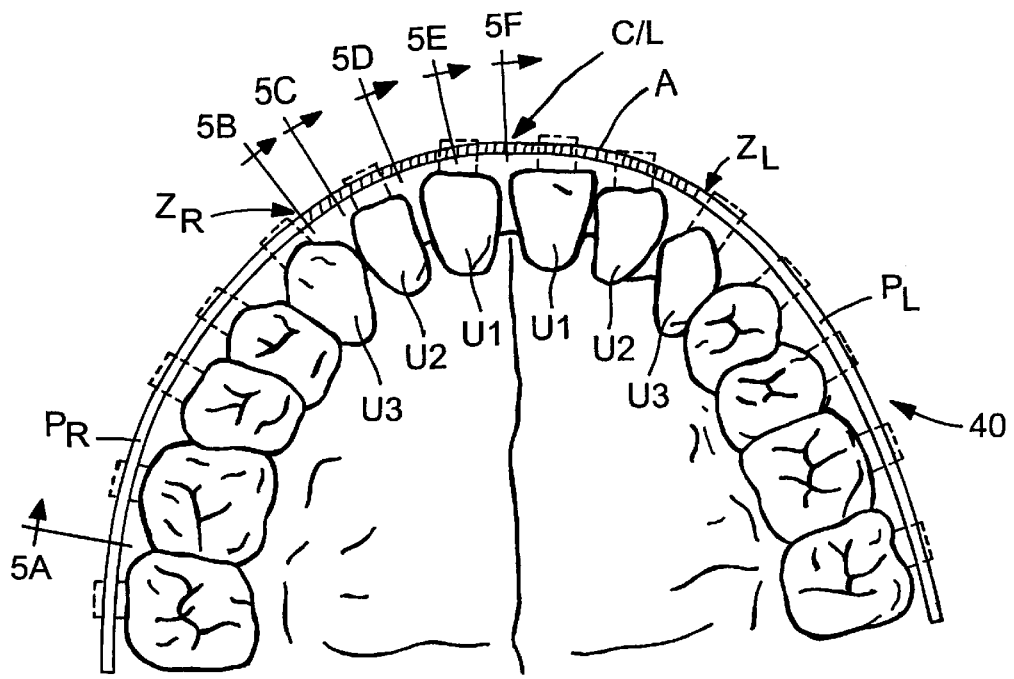
FIG. 4 is a plan view of an embodiment of the inventive torqued archwire shown relative to the set of upper permanent teeth illustrated in FIG. 1 and corresponding brackets (representationally illustrated in phantom)

Turning now to FIG. 4, there is shown an embodiment of the inventive torqued archwire 40 depicted in relation to the set of upper permanent teeth of FIG. 1 and corresponding edgewise brackets (shown in phantom). The archwire has a torqued active region (A), which overlaps the brackets attached to the four anterior teeth (U1, U2) and is identified, on one of its surfaces, by a colored coating of non-toxic FDA white-listed ink (the hatched region in FIG. 4). At the two distal ends ($Z_L$, $Z_R$) of the active region, the built-in torque decreases to zero. It is at these two precisely located points—referred to hereinafter as the "zero" points—where the transitions from the torqued active region to the untorqued (passive) posterior regions ($P_L$, $P_R$) occur. Each posterior region is preferably untorqued (0°) along its entire length, although either small (and clinically insignificant) positive torque or negative torque can exist in these regions due to unavoidable manufacturing tolerances (±2°).

In accordance with an important aspect of the present invention, the torquing of the archwire begins precisely at the "zero" points ($Z_L$, $Z_R$), which are formed in the archwire a predetermined arcuate distance from one another, depending upon the desired "size" of the wire. Since the populace includes persons having different archwidths, it is desirable to provide archwires having active regions of various lengths (i.e., sizes). Active region lengths over a range of about 24–40 mm would be adequate to accommodate almost all persons, and the assignee of this invention, Ortho Specialties, Inc. of Hickory Hills, Ill., presently markets torqued nitinol archwires having three different active region lengths—28 mm, 34 mm and 38 mm. For any given person, an appropriately-sized torqued archwire should be long enough that, upon insertion into the edgewise bracket slots, each of its "zero" points lies in the space between brackets attached to corresponding adjacent lateral and cuspid teeth.

Referring again to FIG. 4 and proceeding mesially from each of the two "zero" points, the amount of torque built into the archwire increases to a maximum value at the centerline (C/L) of the active region. This centerline of the archwire, which is typically identified by a visual indicator (such as a scribe line or a small ink mark), is intended to be positioned in the space between the brackets on the two central teeth (U1) during treatment.

In order to compensate for typically-occurring slot play, the maximum torque value at the centerline is set in the range of about 21–45°, and that value is substantially maintained (i.e., within about 1–2°) across the central teeth. This range of 21–50° has been found to provide desirable results. It has been further found that setting the maximum torque in a range of 23–32° yields especially desirable results. This range is presently the most preferred because it has been determined to be the torque which makes up for torque losses due to deviation angles between the wire and bracket and torque losses due to manufacturing deviations.

In order to ensure that significant torque force is provided by the wire to the two lateral teeth (U2), it is important for the torque built into the archwire to increase rapidly within a short arcuate distance (i.e., about 5 mm) mesial from the "zero" points. Preferably, the torque value at a distance of 3 mm from the "zero" points should be about 5°, and should be at least about 8° at a distance of 5 mm from the "zero" points.

Figure 5:
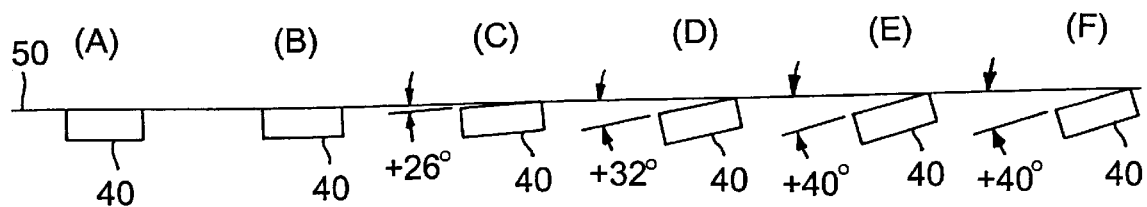
FIGS. 5A through 5F are enlarged, cross-sectional views of the archwire of FIG. 4 taken, respectively, along the lines 5A through 5F, illustrating those views in angular relation to an imaginary plane.

FIGS. 5A–5F show several enlarged, cross-sectional views of the torqued archwire of FIG. 4, taken at various points along one half of the wire (beginning in the right posterior region ($P_R$) and proceeding mesially to the centerline (C/L)). The archwire and brackets are selected in conjunction with one another in order to provide a needed effective torque θ. In FIG. 5A, the archwire is essentially flat (or untorqued), and thus defines an imaginary plane 50 against which the other cross-sectional views can be angularly compared. FIG. 5B is taken at the right "zero" point ($Z_R$), and accordingly there is still no torque built into the wire. FIG. 5C is taken at a point approximately 2–2.5 mm mesial to the "zero" point. Here the built-in torque is about 20°. In the cross-section of FIG. 5D, taken at a point approximately midway between the "zero" point and the centerline, the torque has increased to about 40°. FIG. 5E shows that the torque at a point corresponding to the bracket on the central tooth has increased to about 30°. Finally, at the centerline of the archwire, as shown in FIG. 5F, the built-in torque is also about 30°. These values are exemplary, and other built-in torque values may be used as needed. In an embodiment, the built-in torque values and brackets can be selected to result in a generally uniform effective torque value among sections A–F.

Although not illustrated, it will be appreciated that the inventive archwire is manufactured so that the torques along the left half of the archwire will essentially mirror the right half torques shown in FIGS. 5A–5F.

Since commercial brackets are designed with archwire slots of several sizes (specifically, 0.018, 0.020 and 0.022 inch), it is desirable to provide torqued archwires in several "diameter" sizes so as to minimize slot play. Ortho Specialties, Inc. currently markets three different diameter sizes of torqued, rectangular nitinol archwire: 0.016×0.022 inch (for use with brackets having 0.018 inch slots), 0.018× 0.025 inch (for 0.020 inch slots) and 0.019 ×0.025 inch (for 0.022 inch slots). Wires with each of these diameters are currently provided in the three sizes of anterior arch (i.e., active region) discussed above: 28 mm, 34 mm and 38 mm.

The torqued nitinol (preferably thermally-activated, "martensitic") archwires of Ortho Specialties, Inc. are manufactured in accordance with a multi-step process. For example, a 0.019×0.025 inch torqued nitinol archwire with a 38 mm active region is made by starting with a straight 0.019×0.025 inch nitinol wire. This straight wire is clamped at two points precisely 38 mm apart (the desired "zero" points), and the "active" segment is then simultaneously heated to between 800–1100° F. (depending upon the specific nickel titanium alloy used) and twisted. The degree of twisting is microadjusted until the torque set into the straight wire is approximately 2–3° greater than the value ultimately desired for the finished archwire (e.g., about 32–34° if an archwire with a maximum torque of 30–31° is desired).

The torqued straight wire is then reheated (again to 800–1100° F.) and is slide pressed in a well-known manner between two opposing plates, which have machined into them, respectively, male and female members defining the desired arcuate configuration. During this heating and pressing (bending) step, the posterior segments ($P_L$, $P_R$) are heat set to be flat (i.e., to have 0° torque), and the residual torque in the active segment diminishes slightly because the nitinol relaxes. The natural result of this step is an archwire having a torqued active region as shown in FIGS. 4 and 5A–5F, with a maximum built-in torque at the centerline and diminishing torque in each direction toward the left and right "zero" points ($Z_L$, $Z_R$).

Following the bending step, the posterior segments are trimmed to a bio-correct size for patient use, and the torqued archwire is finally burnished, washed, polished, washed again and marked (at the active region and the centerline) with FDA white-listed ink.

As can be seen from the foregoing detailed description, the present invention provides an improved titanium-based, torqued archwire in which built-in torque is limited to a segment of the wire that, in proper use, corresponds to the brackets attached to a patient's anterior teeth. The torque varies across this anterior segment, but is nevertheless substantial for not only the central teeth, but also for the lateral teeth due to the formation of very short transition zones across which the torque increases from 0° (at a "zero" point) to 8° or more.

Although the invention is described herein in connection with various preferred embodiments, there is no intention to limit the invention to those embodiments. Rather, it should be understood that various changes and modifications to the preferred embodiments will be apparent to those skilled in the art, and that such apparent changes and modifications may be made without departing from the spirit and scope of the present invention and without diminishing its attendant advantages. Therefore, the appended claims are intended to cover such changes and modifications.

What is claimed is:

1. An improved archwire of the type having a substantially rectangular cross-section which, in conjunction with a set of orthodontic brackets having slots to edgewise receive the archwire, applies torque forces to selected teeth, the archwire comprising: a continuous, elongated member of titanium-based alloy formed to have a plurality of segments, including, a curved anterior segment having a centerpoint, which segment, upon insertion into corresponding bracket slots, extends substantially parallel to the four central and lateral teeth with the centerpoint positioned between the brackets on the two central teeth; first and second transition segments, each extending distally from a respective end of the anterior segment; and first and second posterior segments each extending distally from a respective distal end of one of the first and second transition segments; wherein the anterior segment has a built-in torque which varies over the length of the segment, the torque attaining a maximum value at the centerpoint and through a portion of the anterior segment which extends substantially through the slots of at least the two central teeth brackets and then decreasing to a value of about 5° at each end of the anterior segment, each of the posterior segments has approximately 0° built-in torque, and each transition segment has a length whereby, upon insertion of the archwire into the bracket slots, the entire transition segment is positioned between the brackets on corresponding adjacent lateral and cuspid teeth, the transition segments each having a built-in torque which varies from about 0° at the distal end to about 5° at the mesial end, wherein the improvement comprises: said maximum value of said torque having a range of about 21–50°.

2. The archwire of claim 1, wherein the maximum value of said torque has a range of about 23–32°.

3. The archwire of claim 1, wherein the anterior segment and the first and second transition segments have a combined arcuate length in a range of about 24–40 mm.

4. The archwire of claim 1, wherein the length of each of the transition segments is less than 5 mm.

5. The archwire of claim 4, wherein the length of each of the transition segments is in a range of about 2–3 mm.

6. The archwire of claim 1, wherein the portion of the wire comprising the anterior segment and the first and second transition segments is marked with non-toxic ink.

7. An improved archwire of substantially rectangular cross-section which, in conjunction with a set of orthodontic brackets having slots to edgewise receive the archwire, applies torque forces to selected teeth, the archwire comprising: an elongated member of titanium-based alloy including an active anterior region, the active anterior region having built-in torque and a predetermined arcuate length delimited by a pair of zero points on the member at which the built-in torque diminishes from a positive value to 0°; wherein the built-in torque is at least about 8° at respective points within the active anterior region which are 5 millimeters mesial to the two zero points, and increases to a maximum value at a centerpoint of the active anterior region; and wherein the built-in torque at all points along the member distal to the zero points is approximately 0°, wherein the improvement comprises said maximum value having a range of about 21–50°.

8. The archwire of claim 7, wherein the maximum value has a range of about 23–32°.

9. The archwire of claim 7, wherein the active anterior region has an arcuate length in a range of about 24–40 mm.

10. The archwire of claim 7, wherein the active anterior region is marked with non-toxic ink.

11. An improved archwire of the type which, in cooperation with a set of orthodontic brackets having bracket slots which accept the archwire, applies torque forces to selected teeth, the archwire comprising: a continuous, elongated member of titanium-based alloy formed to have a plurality of segments, including, a curved anterior segment of substantially rectangular cross-section having a centerpoint, which segment, upon insertion into corresponding bracket slots, extends substantially parallel to the four central and lateral teeth with the centerpoint positioned between the brackets on the two central teeth; first and second transition segments of substantially rectangular cross-section, each extending distally from a respective end of the anterior segment; and first and second posterior segments, each extending distally from a respective distal end of one of the first and second transition segments; wherein the anterior segment has a built-in torque which varies over the length of the segment, the torque attaining a maximum value at the centerpoint and through a portion of the anterior segment which extends substantially through the slots of at least the two central teeth brackets and then decreasing to a value of about 5° at each end of the anterior segment, each of the posterior segments has approximately 0° built-in torque, and each transition segment has a length whereby, upon insertion of the archwire into the bracket slots, the entire transition segment is positioned between the bracket o corresponding adjacent lateral and cuspid teeth, the transition segments each having a built-in torque which varies from about 0° at the distal end to about 5° at the mesial end, wherein the improvement comprises:

said maximum value having a range of about 21–50°.

12. The archwire of claim 11, wherein the maximum value has a range of about 23–32°.

13. The archwire of claim 11, wherein the anterior segment and the first and second transition segments have a combined arcuate length in a range of about 24–40 mm.

14. The archwire of claim 11, wherein the portion of the wire comprising the anterior segment and the first and second transition segments is marked with non-toxic ink.

15. An improved archwire of the type which, in cooperation with a set of orthodontic brackets has slots for accepting the archwire, applies torque forces to selected teeth, the archwire comprising: an elongated member of titanium-based alloy including an active anterior region of substantially rectangular cross-section, the active anterior region having built-in torque and a predetermined arcuate length delimited by a pair of zero points on the member at which the built-in torque diminishes from a positive value to 0°; wherein the built-in torque is at least about 8° at respective points within the active anterior region which are 5 millimeters mesial to the two zero points, and increases to a maximum torque at a centerpoint of the active anterior region; and wherein the built-in torque at all points along the archwire distal to the zero points is approximately 0°, wherein the improvement comprises:

said maximum torque being in a range of about 21–50°.

16. The archwire of claim 15, wherein the maximum value has a range of about 23–32°.

17. The archwire of claim 15, wherein the active anterior region has an arcuate length in a range of about 24–40 mm.

18. The archwire of claim 15, wherein the active anterior region is marked with a non-toxic ink.

* * * * *